(12) United States Patent
Parikh et al.

(10) Patent No.: US 9,471,985 B2
(45) Date of Patent: Oct. 18, 2016

(54) TEMPLATE-LESS METHOD FOR ARBITRARY RADIOPAQUE OBJECT TRACKING IN DYNAMIC IMAGING

(71) Applicant: MATERIALS ENGINEERING AND PACKAGING, LLC, St. Louis, MO (US)

(72) Inventors: Parag J. Parikh, St. Louis, MO (US); Hanlin Wan, St. Louis, MO (US)

(73) Assignee: MATERIALS ENGINEERING AND PACKAGING, LLC, St. Louis, MO (US)

(*) Notice: Subject to any disclaimer, the term of this patent is extended or adjusted under 35 U.S.C. 154(b) by 0 days.

(21) Appl. No.: 14/449,046

(22) Filed: Jul. 31, 2014

(65) Prior Publication Data

US 2015/0254859 A1    Sep. 10, 2015

Related U.S. Application Data

(60) Provisional application No. 61/860,902, filed on Jul. 31, 2013.

(51) Int. Cl.
*G06K 9/00*    (2006.01)
*G06T 7/00*    (2006.01)
*A61N 5/10*    (2006.01)

(52) U.S. Cl.
CPC ........... *G06T 7/0044* (2013.01); *A61N 5/1049* (2013.01); *G06T 2207/10081* (2013.01); *G06T 2207/10116* (2013.01); *G06T 2207/30004* (2013.01); *G06T 2207/30204* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,769,789 A * | 6/1998 | Wang | ..................... | A61B 19/52 382/131 |
| 5,799,099 A * | 8/1998 | Wang | ..................... | A61B 19/52 382/131 |
| 5,902,239 A * | 5/1999 | Buurman | ................. | A61B 6/12 600/427 |
| 6,381,485 B1 * | 4/2002 | Hunter | ................... | A61B 19/52 324/244 |
| 6,560,354 B1 * | 5/2003 | Maurer, Jr. | ........... | G06T 7/0028 128/922 |
| 6,668,083 B1 * | 12/2003 | Verdonck | ................. | G06T 7/60 382/128 |
| 2013/0006036 A1 * | 1/2013 | Raleigh | ................ | A61N 5/1049 600/1 |
| 2014/0005527 A1 * | 1/2014 | Nagarkar | ................ | A61B 5/05 600/424 |

* cited by examiner

*Primary Examiner* — Anand Bhatnagar
(74) *Attorney, Agent, or Firm* — Vista IP Law Group, LLP

(57) ABSTRACT

A method for localizing a fiducial marker in a medical image includes: obtaining the medical image; and performing an analysis, using an analysis unit, to localize the fiducial marker in the medical image; wherein the fiducial marker is localized by the analysis unit without use of a marker template.

35 Claims, 9 Drawing Sheets

TEMPLATE-LESS METHOD FOR ARBITRARY RADIOPAQUE OBJECT TRACKING IN DYNAMIC IMAGING

RELATED APPLICATION DATA

This application claims priority to and the benefit of U.S. Provisional Patent Application No. 61/860,902, filed on Jul. 31, 2013. The entire disclosure of the above application is expressly incorporated by reference herein.

FIELD

The present disclosure relates to a method and system for tracking arbitrary radiopaque objects in dynamic imaging. Particularly, the present disclosure concerns methods and systems that use dynamic programming to execute an iterative tracking algorithm to locate and track fiducial markers in radiation therapy.

BACKGROUND

Dynamic x-ray imaging is used extensively in medicine to provide image guidance to cardiologists, gastroenterologists, pulmonologists, interventional radiologists, orthopedic surgeons and radiation oncologists. Often, a tool or target is visualized during such dynamic x-ray imaging. For example, fluoroscopy is used during cardiac catheterization to visualize the guidewire as it is inserted, and cone-beam computed tomography (CBCT) is used during orthopedic spine procedures to enhance localized placement of screws.

Dynamic x-ray imaging is also used in radiation therapy to maximize the radiation dose distributed to target volumes (e.g., cancerous growths) in a patient's anatomy while minimizing the dose delivered to surrounding tissues. This practice is referred to as image guided radiation therapy (IGRT), and it allows for increased accuracy in distributing targeted radiation doses to complex target volumes. In particular, IGRT provides a feedback loop that enables adjustment of a patient's treatment based on an assessment of the patient's three-dimensional anatomy just prior to radiation beam delivery. This is especially helpful, as a patient's anatomy continually changes due to physiological changes and treatment responses.

In IGRT based radiation therapy, pre-planning computed tomography (CT) data is used to plan dose distributions while markers are used to line up the patient with the pre-planned dose distribution on treatment day. However, complications arise when the target volume in the patient's anatomy is in motion during the treatment. In particular, movement of the target volume during delivery of the radiation beam therapy may result in an underdosing to the target volume (due to its movement away from the radiation beam), and overdosing of the surrounding normal tissue (due to its movement into the radiation beam). Such target volume motion is often experienced in the treatment of lung, liver, and pancreatic cancers where the relevant anatomy moves due to respiratory motion from a patient's breathing. Target volume motion may also be experienced due to other involuntary muscle movements, such as when the target volume is positioned proximate to cardiac or gastrointestinal muscles. Target volume motion can be clinically significant, on the order of 2-3 cm, depending on target volume site and other patient specific circumstances. See S B Jiang, *Technical Aspects of Image-Guided Respiration-Gated Radiation Therapy*; Medical Dosimetry; 31(2):141-151, 141; 2006. As such, target volume movement can cause large differences between the planned and actual dose distributions, including potential damage to essential surrounding tissues and degraded efficacy of the treatment.

Target volume motion errors may be accounted for by setting dose margins during pre-planning. However, without imaging, a treating physician cannot know whether a target volume remains within the pre-planned boundaries. Thus, many physicians will use a gating technique during therapy. One gating technique is the use of a gating window, wherein the delivery of a radiation dose is timed to correspond with the target volume motion such that the radiation dose is delivered only during periods when the target volume is judged to be in a predetermined path of the radiation beam. Another gating technique is beam-tracking, wherein the radiation beam is made to track the movement of the target volume such that the predetermined path of the radiation beam remains aligned with the moving target volume. This is similar to other image guided interventions, where the practitioner may move the tool to intervene at the correct time and position for the imaged object.

Gating techniques account for movement of a target volume by utilizing external or internal motion surrogates to approximate the target volume motion. In particular, an imaging-conducive structure proximate to a target volume, and which is expected to move in a similar manner to the target volume, is selected to serve as a motion surrogate. The movement of the motion surrogate is then monitored and used to derive a projected motion for the corresponding target volume. Gating techniques using external motion surrogates may be practiced with a system such as the Real-time Position Management (RPM) system, available from Varian Medical Systems (Palo Alto, Calif.). However, studies have shown that external motion surrogates do not always correlate well with actual target volume motion, and are dependent on the placement of the external surrogate. Thus, internal motion surrogates, implanted near the target volume, are preferred when possible. Gating techniques using internal motion surrogates may be practiced with a system such as the Real-time Tracking Radiation Therapy (RTRT) system, available from Mitsubishi Electronics Co., Ltd. (Tokyo, Japan). Suitable structures for use as an internal motion surrogate may include the host organ to the target volume; nearby anatomical structures (e.g., the diaphragm or chest wall for a target volume in the lung); radiopaque markers implanted at the target volume; and radioactive tracers introduced to the target volume. Fiducial markers, which, unlike soft tissue target volumes, are radiopaque and can be seen in x-ray images, are perhaps the most widely used internal motion surrogate.

In a typical clinical setting, one or more fiducial markers are implanted on or near the target volume prior to acquisition of the pre-planning CT images. The markers are then used as a motion surrogate for pre-planning a dose distribution that accounts for a target volume movement. On the day of treatment, immediately prior to dose delivery, CBCT images of the patient are taken from different gantry angles, and a reconstructed three-dimensional (3D) volume is generated from the CBCT images to model the patient's internal anatomy. The reconstructed 3D volume is then used in combination with fluoroscopic images to manually align the fiducial marker locations to those in the pre-planning CT, and to position the patient on the treatment couch. The motion of the fiducial markers in the captured images, corresponding to the target volume motion, is used to specify a gating technique for the treatment. For example, in a gating window technique, the motion of the fiducial marker may be used to manually set the gating window (specifying when the radiation beam is on), such that the radiation dose is delivered only when the target volume is within a specified region corresponding to the fixed path of the radiation beam.

Tracking and localization of fiducial markers in the CBCT images is necessary for discerning the motion of the fiducial markers that are used as motion surrogates in specifying a gating technique and pre-planning delivery of a prescribed radiation dose to a patient. Currently, all known methods for monitoring and localizing fiducial markers in CBCT images use a template matching algorithm, or a derivative thereof. Template matching algorithms use CBCT images to identify a fiducial marker based on a priori information relative to the marker shape and size. In particular, template matching algorithms require a pre-loaded template for matching with the CBCT images to identify a fiducial marker having a corresponding shape and size.

A serious limitation of the conventional template matching algorithms, however, is that they often fail to correctly identify fiducial markers in CBCT images when the images have low contrast (e.g., low signal-to-noise ratio), or when the markers are relatively small or of an irregular shape. This limitation is significant as physicians are moving away from gold spheres and cylinders (which normally present high contrast and a symmetrical shape profile) and more towards coiled fiducial markers. In particular, some consider the coiled fiducial markers easier to implant due to the smaller size, as well as less likely to migrate due to their irregular shape. However, these coiled markers present irregular shapes and a lower contrast as compared to the gold spheres and cylinders. Also, when used with a template matching algorithm, these coiled markers require a treatment operator to manually create a reference template corresponding to the irregular shape of the coiled marker, as the coiled marker will take on a unique shape upon insertion. As such, the performance of a conventional template matching algorithm using a coiled marker greatly depends on the quality of the template, and is subject to the introduction of considerable user errors in generating the template.

Accordingly, the currently available methods and systems for marker tracking, which require a priori information such as a pre-loaded template, are expected to yield evermore inconsistent results as the use of irregularly shaped and sized markers becomes more prevalent. Therefore, there remains a need in the art for a marker tracking method and system that is capable of providing consistently reliable results regardless of marker type, shape, size, and orientation.

SUMMARY

The present disclosure relates to an image analysis method and system. In particular, the present disclosure concerns a method and system for tracking arbitrary radiopaque objects of any type, shape, size, and orientation in dynamic imaging, without the necessity for a user generated template. Particularly, the method and system use dynamic programming to execute a dynamic tracking algorithm that locates fiducial markers in fluoroscopic or CBCT projections by minimizing a global energy function that takes into account a fiducial marker grayscale intensity; a fiducial marker position; and a fiducial marker magnitude of motion between successive images. The results of the dynamic tracking algorithm may facilitate targeting during image guided interventions. The method and system are discussed in greater detail below.

The present method and system permit the localization of a fiducial marker in a medical image through the execution of a dynamic programming algorithm, without use of a marker template.

In particular, the present method and system enable an image analysis by the following steps. First, a set of images is manipulated to generate at least one approximated search window in each image such that the at least one approximated search window is located in the vicinity of a point of interest in the images.

A first dynamic analysis is then performed relative to the approximated search windows in the following manner. One or more contrast points are identified within the at least one approximated search window generated in each image. A contract point being a local point having an imaging intensity presenting a peak contrast relative to the imaging intensities of points surrounding the local point. Then a contrast point characteristic identification step is performed to determine, for each contrast point identified in an individual approximated search window in an individual image of the set of images, at least one of the following contrast point characteristics: i) a distance value between the contrast point and a reference point of the individual approximated search window; ii) an imaging intensity value of the contrast point; and iii) a plurality of distance values measuring the distance from the location of the contrast point in the individual approximated search window to the location of each contrast point in the at least one approximated search window in another image of the set of images. The contrast point characteristic identification step is then repeated for the at least one approximated search window in each image of the image set.

A dynamic programming algorithm is executed to calculate a first resultant point for an individual approximated search window in an individual image of the image set. Particularly, the dynamic programming algorithm is executed based, at least in part, on input values corresponding to at least one contrast point characteristic value determined during the contrast point characteristic identification step, with an input value being provided for each contrast point identified in the individual approximated search window. Execution of the dynamic programming algorithm is then repeated for the at least one approximated search window in each image of the image set; and the calculated first resultant point of each approximate search window is stored in a data storage unit.

Then the set of images is again manipulated to generate at least one refined search window in each image such that the at least one refined search window is positioned based on the first resultant point calculated relative to the individual approximated search window for that respective image during the first dynamic analysis.

A second dynamic analysis is then performed relative to the refined search windows by repeating the steps of the first dynamic analysis, though performing the repeated steps in the second dynamic analysis relative to the refined search windows to calculate and store a second resultant point for each refined search window.

A convergence judgment step is the performed in the following manner to judge if a convergence has occurred in the image analysis. First a comparison step is performed comparing the first resultant point calculated for the at least one approximate search window generated an individual image of the image set with the second resultant point calculated for the at least one refined search window generated in the same individual image to determine if the first resultant point and the second result point are identical. The comparison step is then repeated for the first resultant point and the second resultant point calculated for each image of the image set.

A convergence percentage is then calculated by calculating the percent of images of the image set that have a first resultant point and a second resultant point that are identical; and a judgment is made as to whether the calculated convergence percentage satisfies a predetermined convergence threshold. A convergence is deemed to have occurred if the calculated convergence percentage is equal to or above the predetermined convergence threshold, and a convergence being deemed to not have occurred if the calculated convergence percentage is below the predetermined convergence threshold.

If it is deemed in the convergence judgment step that a convergence has occurred, then the identical point identified by the first resultant point and the second resultant point in each image of the image set is deemed to be the point of interest. Otherwise, if it is deemed in the convergence judgment step that a convergence has not occurred, then image manipulating step; the further dynamic analysis step; and the convergence judgment step are repeated to calculate and store a third resultant point for each further refined search window, and to judge convergence in the image analysis by comparing the third resultant points to the second resultant points.

The image manipulating step; the further dynamic analysis step; and the convergence judgment step are continually repeated until a convergence is deemed to have occurred in the convergence judgment step.

In the foregoing process, the contrast point may be a local minimum point, having a minimum imaging intensity relative to the imaging intensities of points surrounding the local point; or a local maximum point, having a maximum imaging intensity relative to the imaging intensities of points surrounding the local point.

A method for localizing a fiducial marker in a medical image includes: obtaining the medical image; and performing an analysis, using an analysis unit, to localize the fiducial marker in the medical image; wherein the fiducial marker is localized by the analysis unit without use of a marker template.

Optionally, the method further includes determining a search window of the medical image.

Optionally, the search window is determined based on a source-object-imager geometry.

Optionally, the search window is determined based on a previously obtained analysis result.

Optionally, the act of performing the analysis comprises identifying one or more minima in the search window.

Optionally, the one or more minima in the search window are identified based on an intensity contrast with a surrounding background intensity.

Optionally, the act of performing the analysis further comprises determining a cost function.

Optionally, the act of performing the analysis further comprises minimizing the cost function.

Optionally, the cost function comprises a compound cost function.

Optionally, the cost function includes a component representing a rescaled grayscale intensity at a minima in the search window.

Optionally, the cost function includes a component representing a distance from a reference location in the search window to a minima in the search window.

Optionally, the cost function includes a component representing a distance between a minima in the search window of the medical image and a minima in another search window of a successive medical image.

Optionally, the cost function includes a first component representing a rescaled grayscale intensity at a minima in the search window, a second component representing a distance from a reference location in the search window to the minima in the search window, and a third component representing a distance between the minima in the search window of the medical image and a minima in another search window of a successive medical image.

Optionally, the act of minimizing the cost function results in a determination of a marker position for the fiducial marker.

Optionally, the method further includes repeating the act of performing the analysis to determine an additional marker position for the fiducial marker.

Optionally, the method further includes comparing the marker position with the additional marker position.

Optionally, the act of performing the analysis comprises identifying one or more maxima in the search window.

Optionally, the act of performing the analysis further comprises determining a cost function and maximizing the cost function.

An apparatus for localizing a fiducial marker in a medical image includes: a processing unit configured to obtain the medical image, and performing an analysis to localize the fiducial marker in the medical image, wherein the processing unit is configured to localize the fiducial marker without use of a marker template; and a medium for storing a position of the fiducial marker.

Optionally, the processing unit is further configured to determine a search window of the medical image.

Optionally, the processing unit is configured to perform the analysis by identifying one or more minima in the search window.

Optionally, the processing unit is configured to identify one or more minima in the search window based on an intensity contrast with a surrounding background intensity.

Optionally, the processing unit is configured to perform the analysis further by determining a cost function.

Optionally, the processing unit is configured to perform the analysis further by minimizing the cost function.

Optionally, the cost function comprises a compound cost function.

Optionally, the cost function includes a component representing a rescaled grayscale intensity at a minima in the search window.

Optionally, the cost function includes a component representing a distance from a reference location in the search window to a minima in the search window.

Optionally, the cost function includes a component representing a distance between a minima in the search window of the medical image and a minima in another search window of a successive medical image.

Optionally, the cost function includes a first component representing a rescaled grayscale intensity at a minima in the search window, a second component representing a distance from a reference location in the search window to the minima in the search window, and a third component representing a distance between the minima in the search window of the medical image and a minima in another search window of a successive medical image.

Optionally, the act of minimizing the cost function results in a determination of a marker position for the marker.

Optionally, the processing unit is further configured to repeat the analysis to determine an additional marker position for the fiducial marker.

Optionally, the processing unit is further configured to compare the marker position with the additional marker position.

Optionally, the processing unit is configured to perform the analysis by identifying one or more maxima in the search window.

Optionally, the processing unit is configured to perform the analysis further by determining a cost function and maximizing the cost function.

A method for image analysis includes:

I) manipulating a set of images to generate at least one approximated search window in each image such that the at least one approximated search window is located in the vicinity of a point of interest in the images;

II) performing a first dynamic analysis, relative to the approximated search windows by: A) identifying within the at least one approximated search window generated in each image one or more contrast points, a contrast point being a local point having an imaging intensity presenting a peak contrast relative to the imaging intensities of points surrounding the local point; B) performing a contrast point characteristic identification step of determining, for each contrast point identified in an individual approximated search window in an individual image of the set of images, at least one of the following contrast point characteristics: i) a distance value between the contrast point and a reference point of the individual approximated search window; ii) an imaging intensity value of the contrast point; and iii) a plurality of distance values measuring the distance from the location of the contrast point in the individual approximated search window to the location of each contrast point in the at least one approximated search window in another image of the set of images; C) repeating the contrast point characteristic identification step for the at least one approximated search window in each image of the image set; D) executing a dynamic programming algorithm to calculate a first resultant point for an individual approximated search window in an individual image of the image set, wherein the dynamic programming algorithm is executed based, at least in part, on input values corresponding to at least one contrast point characteristic value determined during the contrast point characteristic identification step, with an input value being provided for each contrast point identified in the individual approximated search window; E) repeating execution of the dynamic programming algorithm for the at least one approximated search window in each image of the image set; and F) storing the calculated first resultant point of each approximate search window in a data storage unit;

III) manipulating the set of images to generate at least one refined search window in each image such that the at least one refined search window is positioned based on the first resultant point calculated relative to the individual approximated search window for that respective image during the first dynamic analysis;

IV) performing a second dynamic analysis, relative to the refined search windows by repeating the steps of the first dynamic analysis (II), though performing the repeated steps in the second dynamic analysis relative to the refined search windows to calculate and store a second resultant point for each refined search window; and V) performing a convergence judgment step to judge if a convergence has occurred in the image analysis by: G) performing a comparison step of comparing the first resultant point calculated for the at least one approximate search window generated an individual image of the image set with the second resultant point calculated for the at least one refined search window generated in the same individual image to determine if the first resultant point and the second result point are identical; H) repeating the comparison step for the first resultant point and the second resultant point calculated for each image of the image set; I) calculating a convergence percentage by calculating the percent of images of the image set that have a first resultant point and a second resultant point that are identical; and J) judging whether the calculated convergence percentage satisfies a predetermined convergence threshold, with a convergence being deemed to have occurred if the calculated convergence percentage is equal to or above the predetermined convergence threshold, and a convergence being deemed to not have occurred if the calculated convergence percentage is below the predetermined convergence threshold, wherein, if it is deemed in the convergence judgment step (J) that a convergence has occurred, then the identical point identified by the first resultant point and the second resultant point in each image of the image set is deemed to be the point of interest, and wherein, if it is deemed in the convergence judgment step (J) that a convergence has not occurred, then steps (III), (IV) and (V) are repeated to calculate and store a third resultant point for each further refined search window, and to judge convergence in the image analysis by comparing the third resultant points to the second resultant points.

Optionally, the contrast point is a local minimum point, being a local point having a minimum imaging intensity relative to the imaging intensities of points surrounding the local point.

Optionally, the contrast point is a local maximum point, being a local point having a maximum imaging intensity relative to the imaging intensities of points surrounding the local point.

A computer program product comprises a non-transitory medium storing a set of instructions, an execution of which by a processing unit causes a method for localizing a fiducial marker in a medical image to be performed, the method comprising: obtaining the medical image; and performing an analysis to localize the fiducial marker in the medical image; wherein the fiducial marker is localized by the analysis unit without use of a marker template.

Optionally, the set of instructions comprise an instruction for obtaining the medical image.

Optionally, the set of instructions comprise an instruction for performing the analysis to localize the fiducial marker in the medical image.

Optionally, the set of instructions comprise an instruction for determining a search window of the medical image.

Optionally, the instruction for determining the search window comprises an instruction for determining the search window based on a source-object-imager geometry.

Optionally, the instruction for determining the search window comprises an instruction for determining the search window based on a previously obtained analysis result.

Optionally, the instruction for performing the analysis comprises an instruction for identifying one or more minima in the search window.

Optionally, the instruction for identifying one or more minima in the search window comprises an instruction for identifying the one or more minima in the search window based on an intensity contrast with a surrounding background intensity.

Optionally, the instruction for performing the analysis comprises an instruction for determining a cost function.

Optionally, the instruction for performing the analysis further comprises an instruction for minimizing the cost function.

Optionally, the cost function comprises a compound cost function.

Optionally, the cost function includes a component representing a rescaled grayscale intensity at a minima in the search window.

Optionally, the cost function includes a component representing a distance from a reference location in the search window to a minima in the search window.

Optionally, the cost function includes a component representing a distance between a minima in the search window of the medical image and a minima in another search window of a successive medical image.

Optionally, the cost function includes a first component representing a rescaled grayscale intensity at a minima in the search window, a second component representing a distance from a reference location in the search window to the minima in the search window, and a third component representing a distance between the minima in the search window of the medical image and a minima in another search window of a successive medical image.

Optionally, the instruction for minimizing the cost function comprises an instruction for determining a marker position for the fiducial marker based on a minimization of the cost function.

Optionally, the set of instructions further comprise an instruction for repeating the act of performing the analysis to determine an additional marker position for the fiducial marker.

Optionally, the set of instructions further comprise an instruction for comparing the marker position with the additional marker position.

Optionally, the instruction for performing the analysis comprises an instruction for identifying one or more maxima in the search window.

Optionally, the instruction for performing the analysis further comprises an instruction for determining a cost function and maximizing the cost function.

Other and further aspects and features will be evident from reading the following detailed description of the embodiments.

BRIEF DESCRIPTION OF THE DRAWINGS

Further features and advantages of the embodiments can be ascertained from the following detailed description that is provided in connection with the drawings described below.

DETAILED DESCRIPTION

Various embodiments are described hereinafter with reference to the figures. It should be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

The present disclosure relates to a method and system for tracking arbitrary radiopaque objects of any type, shape, size, and orientation in dynamic imaging, without the necessity for a user generated template. Particularly, the method and system use dynamic programming to execute a dynamic tracking algorithm that locates fiducial markers in fluoroscopic or CBCT projections by minimizing a global energy function that takes into account a fiducial marker grayscale intensity; a fiducial marker position; and a fiducial marker magnitude of motion between successive images. The results of the dynamic tracking algorithm may facilitate targeting during image guided interventions. The method and system are discussed in greater detail below.

The Template-Less Marker Tracking Algorithm

Figure 1:
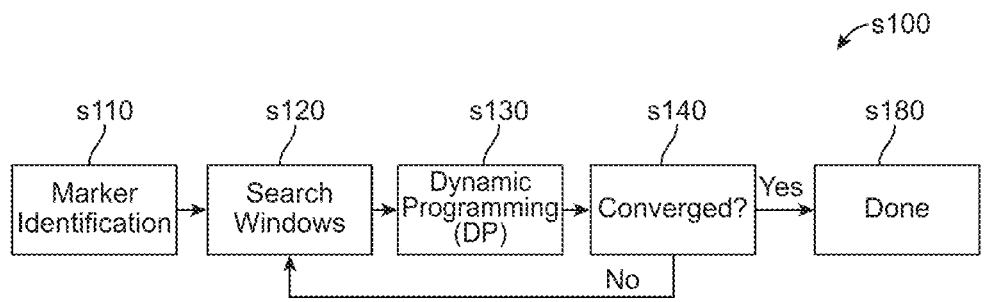
FIG. 1 shows a dynamic programming marker tracking algorithm according to some embodiments.

FIG. 1 shows a generalized process S100 for performance of a template-less marker tracking algorithm according to some embodiments for tracking and localizing a fiducial marker. In a first step s110, an operator manually locates a single point per marker, in the general vicinity of the marker's true location, in two-dimensional 2D images of a patient's anatomy. This is done either by identifying a 3D location (using either pre-planning CT images or a reconstructed CBCT model) and projecting that 3D location to a corresponding 2D location when processing CBCT images; or by setting an initial 2D location when processing the fluoroscopy images. These 2D locations are then accessed in a step s120; and search windows are applied to each of the images based on the 2D locations. The images, with the search windows set therein, then undergo optimization by a dynamic programming algorithm in a step s130. Thereafter, in a step s140, a judgment is made as to whether the dynamic programming analysis in step 130 has resulted in convergence. If it is judged that a convergence has resulted, the process S100 proceeds to a step s180 and ends.

If it is judged at step s140 that a convergence has not occurred, then the process S100 returns to step s120. Upon returning to step s120, refined search windows are applied to each of the images based on the results of the dynamic programming analysis performed in step s130 during the prior iteration of the process S100. Steps s130 and s140 are then repeated in similar fashion to their execution during the prior iteration of the process S100. The process S100 continues to repeat in this manner until a judgment is made at step s140 that convergence has been achieved, such that the process S100 will then proceed to the step s180 and end.

In the first step s110, a system 300 accesses a set of 2D images stored in a local storage unit 350; and a system user manually locates and identifies a single point per marker in at least one image of the set. The 2D images may be projections from CBCT acquisition or fluoroscopy; and the 3D fiducial marker locations are acquired by the user from pre-planning CT images and imported to the storage unit 350 through a user interface 310, which communicates with a controller 390 that controls communications between the various components of the system 300. Alternatively, an initial location for the markers in the 2D images may be acquired from 2D pre-planning imaging having the same orientation. After the user manually identifies a single point per marker in at least one image of the image set, the system 300 will automatically populate the search windows in the images.

Figure 2:
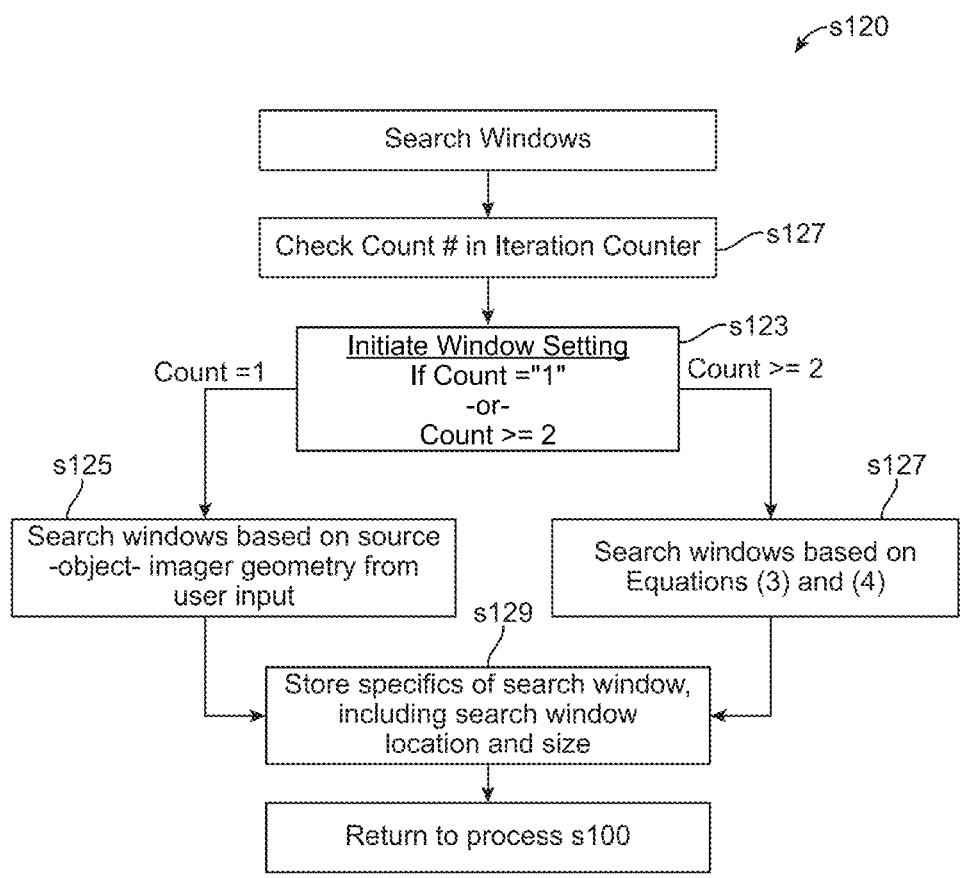
FIG. 2 shows a search window step of the marker tracking algorithm in FIG. 1.

FIGS. 2-5 further illustrate step s120. In particular, as shown in FIG. 2, in a first step s121 a determination is made as to the count of the current iteration for the process S100 by referencing an iteration counter 320. In a first iteration of the process, the iteration counter 320 will indicate "1", reflecting that the current iteration of the process S100 is a first iteration. Each time the process S100 repeats, the iteration counter 320 is updated to reflect the present iteration being initiated at the search window step s120 (as will be discussed below).

Figure 3A:
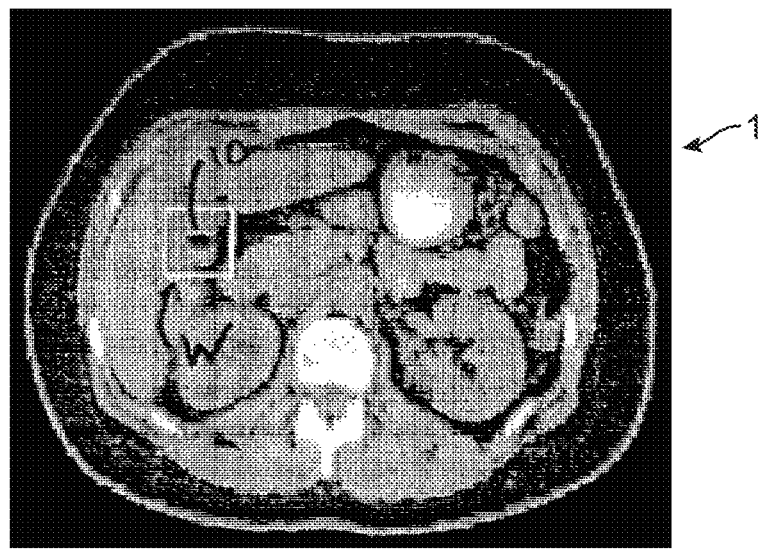
FIGS. 3A-3B show exemplary images processed by the marker tracking algorithm of FIG. 1.
Figure 3B:
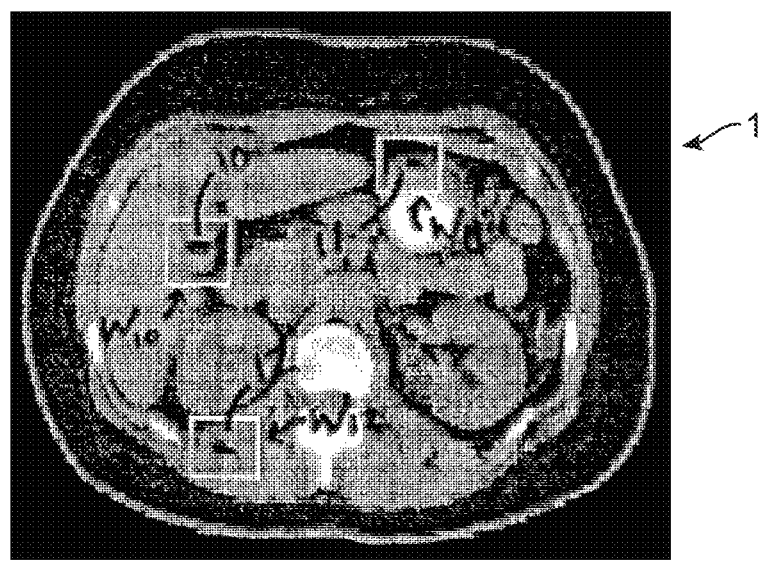

In a step s123, a search window setting unit 330 initiates a window setting operation based on the count number retrieved from the iteration counter 320. If the count number reflects that the current iteration is the first iteration (count="1"), then the process proceeds to a step s125 wherein the user selected location is used to create a search window W based on the source-object-imager geometry. Alternatively, if the count number indicates that the current iteration is not the first iteration (count≥"2"), then the process will proceed to a step s127 wherein the window setting unit 330 will retrieve stored dynamic programming analysis results obtained during a prior iteration of the process S100 from the output of a prior executed step s130; and use the retrieved data to generate the search windows W for each marker. In both of the step s125 and s127, a separate search window W is generated in a manner to correspond with an approximate location of each fiducial marker 10, as shown in FIGS. 3A and 3B.

In step s125, when generating the first search windows W, it is assumed that all of the CBCT images share a common isocenter (the point in space through which the central ray of the radiation dose beams passes). Therefore, a fixed marker point (r; θ; z), for a single marker in a polar 3D object space, is projected to the image point (x; y) for each gantry angle Ø according to the following relationships, as expressed by equations (1) and (2):

$$x = r\cos\theta\cos\phi + r\sin\theta\sin\phi \quad (1)$$
$$= r\cos(\phi - \theta)$$
$$y = z \quad (2)$$

Figure 14A:
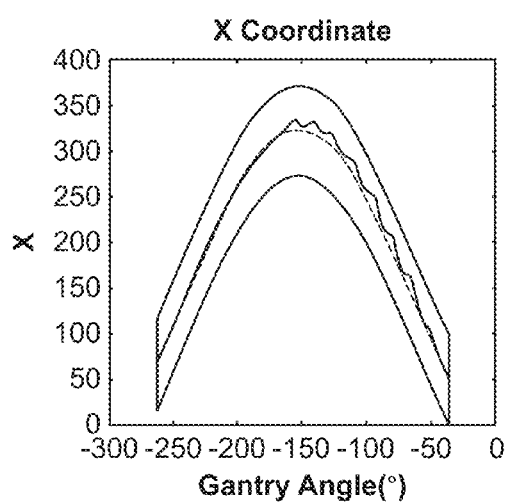
FIGS. 14A and 14B show relationship of gantry angles in accordance with some embodiments.
Figure 14B:
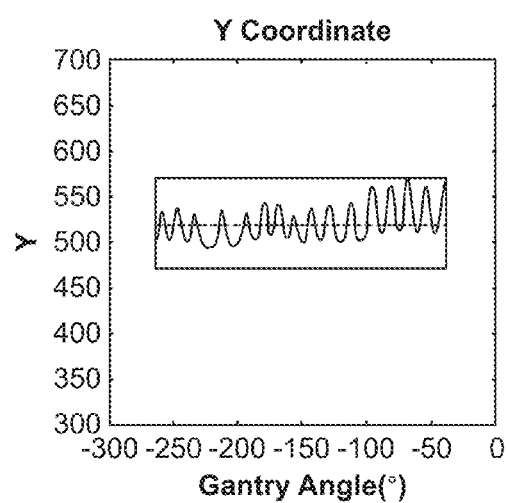
Figure 15:
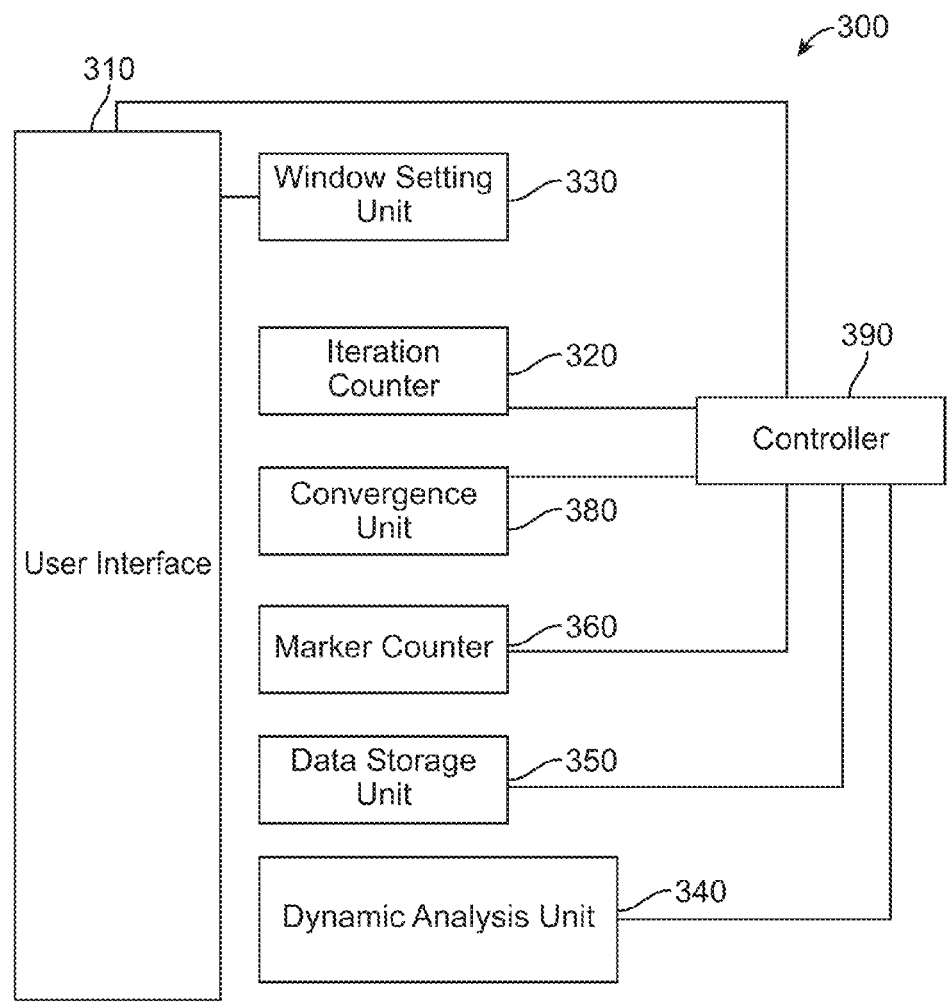
FIG. 15 shows a system for executing algorithms in accordance with some embodiments.

Equations (1) and (2) state that a static marker will have a constant value in the y-axis of the projected images for all gantry angles Ø and will move in a sinusoidal path in the x-axis as the gantry angle Ø varies, as illustrated in FIGS. 14A and 14B. In particular, the graphs in FIGS. 14A and 14B show the marker locations in solid lines, with search windows shown in the shaded region, and the center of the search windows shown by the dashed lines. In CBCT images where a marker may move due to respiratory motion, the y-coordinate will fluctuate corresponding to superior-inferior motion, while the x-coordinate will deviate from the sinusoidal path, corresponding to anterior-posterior and left-right motions.

In step s129, when iteration counter 320 is greater than 1, the results from step s130 are used to construct the new search windows using equations (3) and (4), where (r, θ) represent the marker position in polar coordinates, Ø is the angle of the imager; and x and y are locations in the image:

$$x = r'\cos(\phi - \theta') \quad (3)$$
where,
$$r' = \sqrt{r^2 + r_0^2 - 2rr_0\cos(\theta - \theta_0)}$$
$$\theta' = \arctan\frac{r\sin\theta - r_0\sin\theta_0}{r\cos\theta - r_0\cos\theta_0}.$$
$$y = y_0 + a \quad (4)$$

These equations assume that all markers will move as a rigid unit in all images. Since this assumption is only used to construct the search windows $W_{10}/W_{11}/W_{12}$ for each marker, small amounts of non-rigidity will not affect the results.

In equation (3), the x-coordinate and the gantry angle Ø are stacked column vectors formed by concatenating those vectors for each marker 10/11/12; $r_0$ and $\theta_0$ are the original stacked 3D locations of all the markers 10/11/12; and r and e are the two free parameters to be fitted using a nonlinear, least squares solver. Equation (3) ensures that the x-coordinate centers of each search window $W_{10}/W_{11}/W_{12}$ is a rigid transformation from the known locations of the static markers 10/11/12.

In equation (4), the y-coordinate centers of each search window $W_{10}/W_{11}/W_{12}$ are similarly rigidly constrained, where the mean y-coordinate over all gantry angles Ø for each marker is simply the foregoing translation. Particularly, the y-coordinate and $y_0$ are stacked column vectors of the current and original mean y-coordinates, respectively; and a is the single free parameter to be fitted using a least squares solver. All search windows $W_{10}/W_{11}/W_{12}$ are centered on the x and y locations from equations (3) and (4). A suitable search area SA defined by the search window W may be 100×100 pixels (2.28×2.28 cm), though search windows defining search areas of other sizes may be used.

When the process S100 is performed for a target volume that is in motion, a fiducial marker 10, that is positioned proximate to the target volume, will likewise be in motion. In such instances, it may be necessary to adjust the positioning of the search window W based on the marker movement.

Figure 4A:
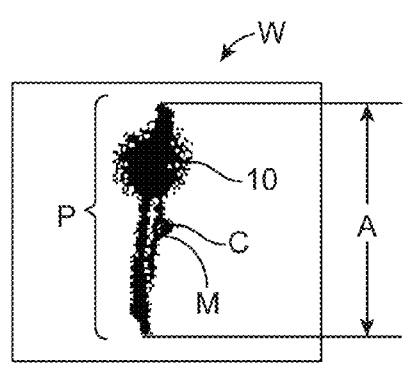
FIGS. 4A, 4B and 5 show search windows for processing images according to the marker tracking algorithm in FIG. 1.
Figure 4B:
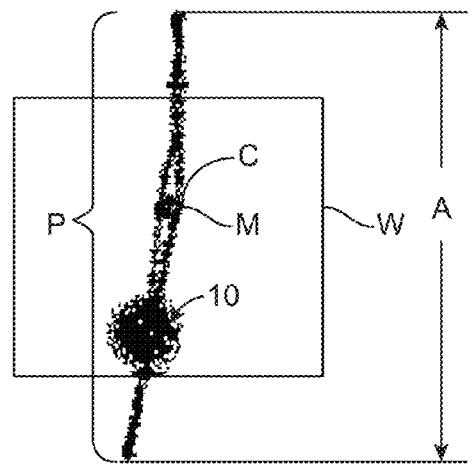

When, as shown in FIG. 4A, the amplitude A of the marker movement is sufficiently small that it will not move outside the search window W, the search window W may be positioned according to the foregoing equations (3) and (4), though with its center C located proximate to an estimated mean location M of the marker movement path P. However, when, as shown in FIG. 4B, the amplitude A of the marker movement is of a sufficiently large length that it is likely the marker 10 will move outside the search window W, a model of the approximate marker motion is needed. Such a marker motion model may be generated by importing external surrogate movement data from an external marker tracking system (e.g., Varian's RPM system).

Figure 5:
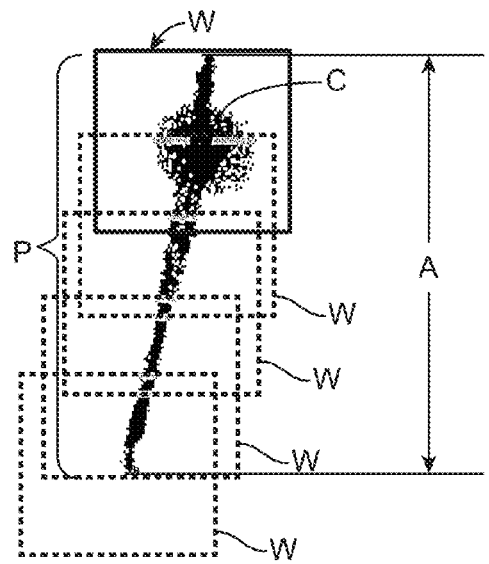

Upon importing such marker movement data, a moving search window W may be generated such that a center C of the moving search window W moves with the projected location of the marker 10, as shown in FIG. 5. In particular, when target volume motion, such as respiratory motion, causes large fluctuations in the y-coordinate location, a marker 10 may move too great a distance within the search window W for performance of the dynamic analysis (discussed below relative to step s130) with a desirable efficiency. Therefore, it is best to model any such target volume motion and to move the y-coordinate centers of the search window W, or each search window $W_{10}/W_{11}/W_{12}$ accordingly.

In one example, Varian's RPM system may be used to record a target volume movement using an external tracking system; and the y-coordinate relationship expressed in equation (4) may be replaced with the following relationship expressed in equation (5):

$$y = a_0 y_{rpm} + a_1 \qquad (5)$$

In equation (5), $a_0$ and $a_1$ are the scaling and translation parameters of the RPM locations; with $a_0$ being the same for all markers $W_{10}/W_{11}/W_{12}$, while $a_1$ may differ between markers $W_{10}/W_{11}/W_{12}$. The parameters $a_0$ and $a_1$ are also fitted using a least squares solver.

After a search window W has been generated for each marker point, the specifics of each of the foregoing, including the location and dimensions of each search window, is recorded to the data storage unit 350 in a step s129. The process then proceeds to s130.

Figure 6:
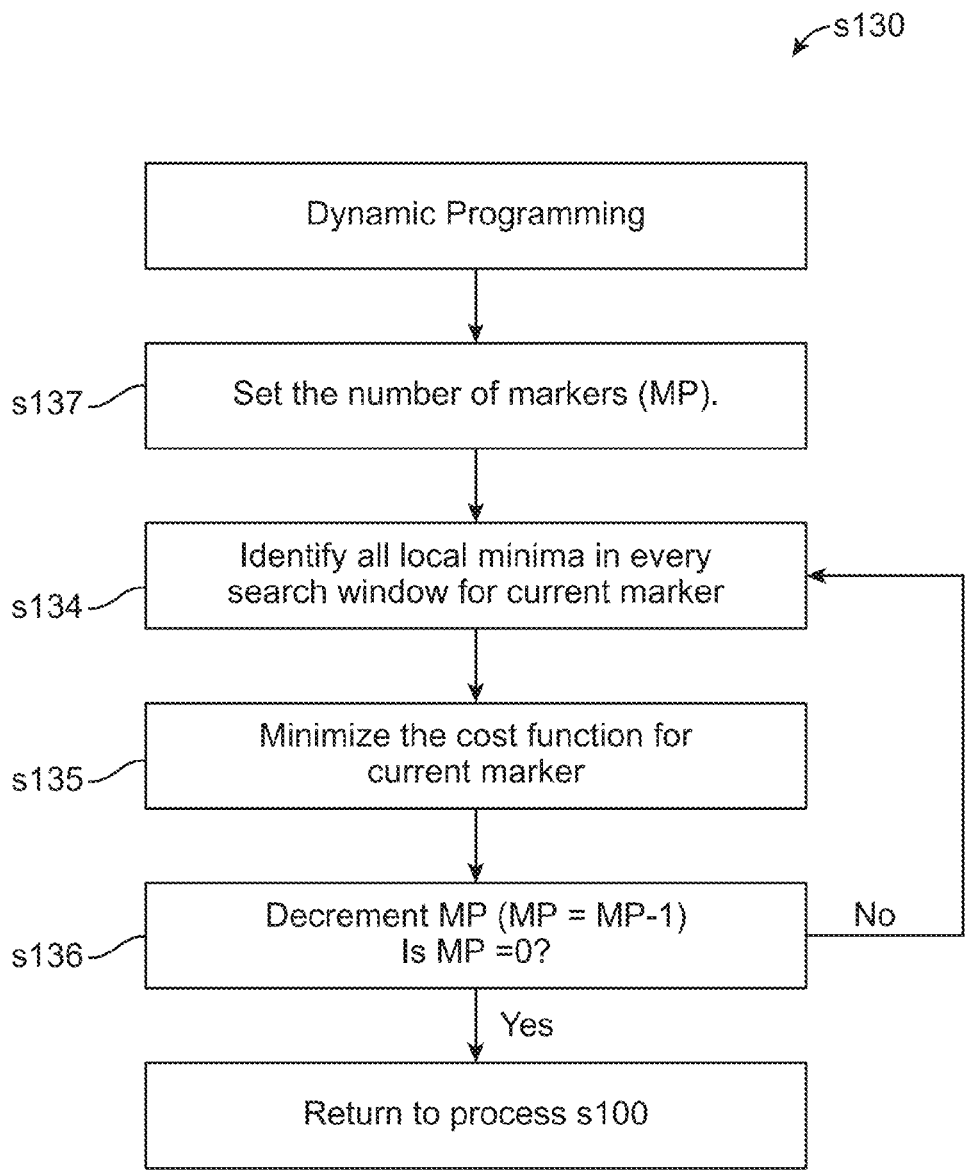
FIG. 6 shows a dynamic programming step of the marker tracking algorithm in FIG. 1.

After setting a search window W for each marker 10 in the step s120, a dynamic analysis unit 340 executes a dynamic programming at step s130, as illustrated by FIG. 6. The dynamic analysis unit 340 will run the dynamic programming algorithm for each marker, one at a time. When tracking multiple markers 10/11/12, as illustrated by FIG. 3B, the dynamic programming will be applied sequentially to each marker 10/11/12 individually. The dynamic analysis unit will determine all possible marker locations in each search window of each image, and then store these results in the data storage unit 350. These possible marker locations correspond to local minima in the images within the search windows. In particular, since the markers have a lower intensity value than the background, markers can only reside at local minima in the image.

In particular, in a step s131, the dynamic analysis unit 340 will access the data storage unit 350 to retrieve the data stored during the previous step s129; and will set a marker counter 360 to a value MP reflecting the number markers present for tracking in the current process S100. After setting the marker value MP, the process proceeds to step s134.

In a step s134, the dynamic analysis unit 340 will identify all local minima in a given search window of each image that corresponds to a particular marker that is to be tracked in the current process S100. Particularly, the dynamic analysis unit 340 will determine all possible marker locations in the corresponding search window for a particular marker, in each image of the image set, by identifying local minima in the search widow. The local minima may be identified based on an intensity contrast with the surrounding background intensity. These identified local minima are used to approximate possible marker locations on the understanding that the markers will have a lower intensity value than the background, and thus the markers can only reside at local minima. During step s134, the location and grayscale intensity of each minima in the search window, as determined in each image, will be recorded to the data storage unit 350.

In step s135, the dynamic analysis unit 340 will access the minima data stored in the data storage unit 350 during the step s134 and execute a dynamic programming algorithm based on this data. Particularly, the dynamic programming algorithm analyzes the results obtained from searching the limited areas SA, defined by each search window W to minimize a cost function $f(p_1, p_2, \ldots, p_N)$. The limited search area SA decreases the computational complexity and increases the robustness of the dynamic programming algorithm.

Dynamic programming analysis is performed according to the following compound cost function $f(\bullet)$, as represented by equation (6):

$$f(p_1, p_2, \ldots, p_N) = \sum_{i=1}^{N} g(p_i) + \alpha \sum_{i=1}^{N} h(p_i) + \beta \sum_{i=1}^{N-1} k(p_i, p_{i+1}) \qquad (6)$$

where, $$g(p_i) = \sqrt{(x_i - c_x)^2 + (y_i - c_y)^2}$$

$$h(p_i) = I(x_i, y_i)$$

$$k(p_i, p_{i+1}) = \sqrt{(x_i - x_{i+1})^2 + (y_i - y_{i+1})^2}$$

Figure 7:
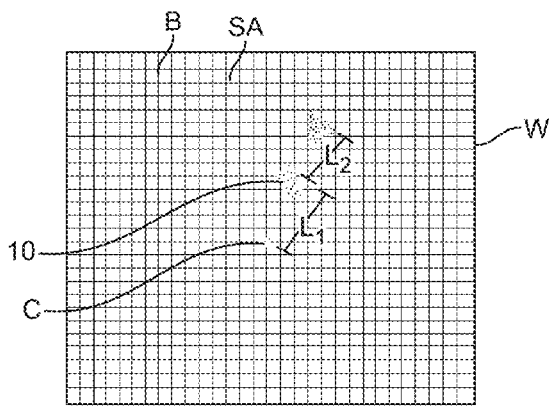
FIG. 7 shows another view of a search window for processing images according to the algorithm in FIG. 1.
Figure 8:
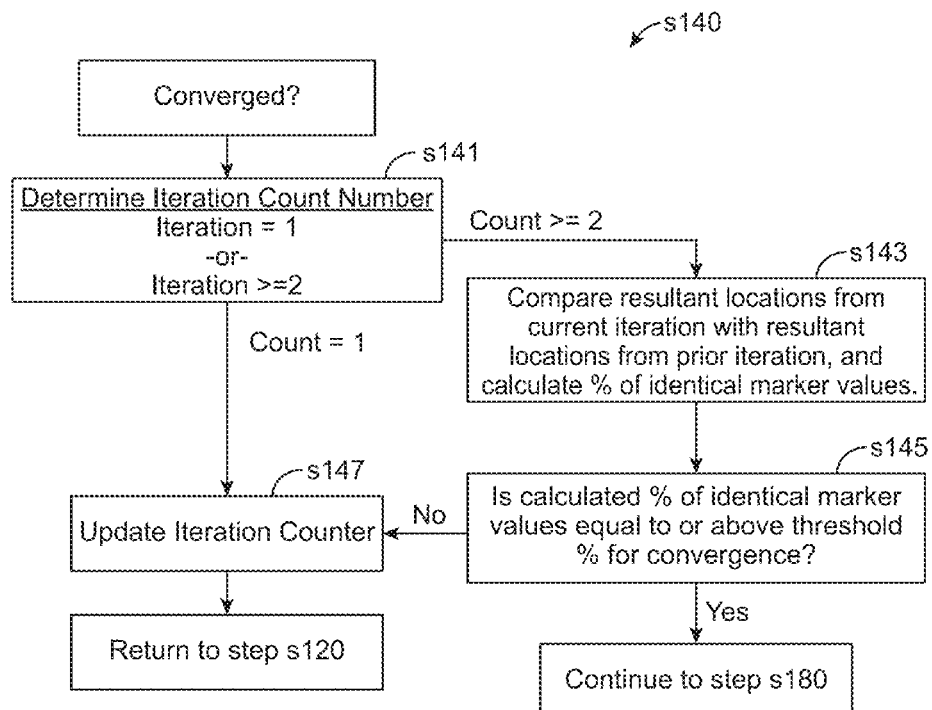
FIG. 8 shows a convergence step of the marker tracking algorithm in FIG. 1.

In equation (6), each $p_i$ is a resultant vector of all the local minima in the current image i; and N is the number of analyzed images. In x-ray images, pixels corresponding to a radiopaque fiducial marker 10 will have a lower intensity than neighboring pixels corresponding to the background B, as illustrated by FIG. 7. Therefore, the marker must correspond to one of the local minima in $p_i$.

As shown by equation (6), the compound cost function f ($\bullet$) is inclusive of a plurality of constituent cost functions g ($\bullet$), h ($\bullet$) and k ($\bullet$). The g ($\bullet$) and h ($\bullet$) cost functions depend only on the current image i; whereas the k ($\bullet$) cost function depends on two immediately successive images (i, and i+1). The h ($p_i$) function represents a rescaled grayscale intensity at the minima, with $I(x_i, y_i)$ linearly rescaled for the search window W, such that the extreme values for the pixels in each $p_i$ are 0 and 1. In this way, because the radiopaque fiducial marker 10 has a lower intensity than the background B, the h ($p_i$) function will force the minimum cost to occur at the lowest intensity pixel. The g ($p_i$) function represents the Euclidean distance L1 (as shown in FIG. 7) from the center C of the search window W to the minima representing a suspected marker 10; and forces the minimum cost to occur when the marker 10 is close to the center C of the search window W. The k ($p_i, p_{i+1}$) function is the Euclidean distance L2 (as shown in FIG. 7) between possible minima $10_i$ and $10_{i+1}$ in immediately successive images (i, and i+1). Since images are normally acquired at a high rate (e.g., 11 Hz, or about 11 images per second), the marker 10 does not move much between successive images; and the k ($p_i, p_{i+1}$) function thus forces the minimum cost to occur when the marker 10 moves the least between successive images.

The coordinates ($c_x$, $c_y$) in equation (6) correspond to the center C of the search window W; and the variables $\alpha$ and $\beta$ are weighting parameters that are determined empirically to balance the need to constrain motion between images with the need to avoid false minima. The parameters $\alpha$ and $\beta$ can be tuned by testing the algorithm on sample data sets. In the experimental tests discussed below, the parameters $\alpha$ and $\beta$ used were $\alpha=10$, and $\beta=35$.

Once equation (6) has been minimized for a given search window in all of the images, there will be generated a set of resultant locations (Rx, Ry) representing a best guess location for the marker in that given search window for each of the images. For example, if the data set includes 400 images, then the execution of the dynamic programming algorithm in step s135 will result in 400 resultant marker locations (Rx, Ry), with each one corresponding to a single image of the 400 image set. In this manner, a marker such as the marker 10 in FIG. 3B would have a resultant value $(R_{10}x, R_{10}y)_1$ for the search window $W_{10}$ in a first image; a resultant value $(R_{10}x, R_{10}y)_2$ for the search window $W_{10}$ in a second image; and a resultant value $(R_{10}x, R_{10}y)_3$ for the search window $W_{10}$ in a third image; and etc. Before exiting the step s135, the generated resultant values are stored in the data storage unit 350.

Then, in a step s136, the dynamic processing unit decrements the marker counter value MP by "1", and judges whether all markers have been tracked (MP="0"), or whether there are further markers requiring tracking (MP≥"1"). If it is judged that all markers have been tracked (MP="0"), then the dynamic programming analysis step s130 ends. If it is judged that there are further markers requiring tracking, then the process returns to step s134.

If returning to step s134, the minima detection and dynamic programming analysis are repeated relative to the next marker. In such instances, where there are multiple markers 10/11/12, the markers 11 and 12 will also have resultant values $(R_{11}x, R_{11}y)_1/(R_{12}x, R_{12}y)_1$; $(R_{11}x, R_{11}y)_2/(R_{12}x, R_{12}y)_2$; and $(R_{11}x, R_{11}y)_3/(R_{12}x, Ry_{12})_3$, and etc., for the respective search windows $W_{11}$ and $W_{12}$ in the first, second and third images respectively. Again, before exiting the step s135 the list of marker locations (Rx, Ry)i are stored in the data storage unit 350. Steps s134-s136 continue to repeat in this fashion until a judgment is made in step s136 that all markers have been tracked (MP="0"), after which the dynamic programming analysis step will end.

In some cases, the dynamic analysis unit 340 may be a specialized unit configured specifically to perform one or more functions described herein. In some embodiments, the dynamic analysis unit 340 may be implemented using hardware, such as an integrated circuit. By means of non-limiting examples, the integrated circuit may be one or more processors, such as one or more FPGA processors, one or more microprocessors, one or more signal processors, one or more ASIC processors, one or more general purpose processors, or any combination of the foregoing, but is specifically configured to be a specialized unit to perform one or more functions described herein. Also, in some cases, the dynamic analysis unit 340 may include both hardware and software.

Although the foregoing example discusses applying minimizing the compound cost function f (•) relative to local minima, the function can also be applied in instances where the intensity values of the marker's correspond to local maxima, by maximized the compound cost function f (•).

In the step s140, a convergence unit 380 accesses the dynamic programming outputs stored in the data storage unit 350 to judge whether convergence has occurred.

In a first step s141, the convergence unit 380 determines whether the current iteration of the process S100 is a first iteration or a second or further iteration, by accessing the iteration counter 320. The iteration count, as carried by the iteration counter 320, reflects the number of times that the steps s120/S130/s140 have been executed in the current performance of the process S100. The iteration counter 320 carries a count of "1" as a default value. If it is judged at step s141 that the current iteration is a first iteration (count="1"), then the convergence unit 380 updates the iteration counter 320 in a step s147 to advance the iteration count by "1", and returns the process to step s120 to initiate a further iteration of the process S100. If it is judged at step s141 that the current iteration is a second or further iteration (count≥"2"), then the process proceeds to step s143 wherein the convergence unit 380 accesses the output values (Rx, R_y)i of the marker locations stored in the data storage unit 350 during the dynamic programming analysis step s130.

In particular, in step s143 of a second or further iteration of the process S100, the convergence unit 380 will access the stored resultant marker locations (Rx, Ry)i that were recorded for each search window, in each image of the complete image set, in both the current iteration of the process S100 and the immediately prior iteration of the process S100. The convergence unit 380 will then compare the individual resultant marker locations (Rx, Ry)i for each given search window in each image of the image from the current iteration of the process S100 against the resultant marker location (Rx, Ry)i for the same search window in the same image from the prior iteration of the process S100. After comparing all corresponding resultant marker locations, the convergence unit 380 will calculate a percentage of identical resultant marker location (Rx, Ry)i between the current iteration and the prior iteration.

In a step s145, it is judged whether a convergence has occurred by determining whether the percentage of identical resultant values between successive iterations, as calculated in step s143, is equal to or greater than a pre-determined percentage threshold. Ideally, convergence will be judged to have occurred when the a threshold of 100% is satisfied, which is indicative that the resultant marker location (Rx, Ry)i for each resultant marker location in each image of the current iteration of the process S100 is found to be identical to the resultant marker location (Rx, Ry)i for each corresponding marker in each corresponding image of the prior iteration of the process S100. In practice, however, due to round-off errors and other small differences, the resultant marker locations are not identical. Therefore, a convergence threshold may be set is set such that if a suitably high percentage of the resultant marker locations (Rx, Ry)i are identical between successive iterations, then convergence will be deemed to have occurred. A suitable percentage of identical resultant marker locations between successive iterations may be between about 95% and about 99%; preferably between about 97.5% and about 99%; and more preferably about 99%.

If it is determined in step s145 that the percentage of identical resultant values between successive iterations, as calculated in step s143, is less than the pre-determined percentage threshold, then the process proceeds to step s147, updates the iteration counter 320 to advance the count by "1", and returns the process to step s120 to initiate a further iteration of the process S100. If, however, it is determined in step s145 that the percentage of identical resultant values between successive iterations, as calculated in step s143, is equal to or greater than the pre-determined percentage threshold, then the process proceeds to step s180 and terminates.

Although the example in FIG. 1 illustrates a process S100 that will repeat indefinitely until convergence is satisfied in step s140 (s145), a system 300 executing the process S100 may be programmed to terminate the process, regardless of convergence, upon the occurrence of a predetermined event. For example, the system 300 may terminate the process S100 after executing a predetermined number of iterations, or the passage of a predetermined period of time, that has been deemed to suggest that: the algorithm will not converge, that the algorithm will require an excessive period of time to converge, or that a computing error has occurred in the system 300.

Experimental Testing

Comparative testing was conducted between a traditional template matching algorithm and the dynamic programming algorithm using a first collection of 37 data sets acquired by CBCT imaging and having 91 markers in total; and a second collection of 329 data sets acquired by fluoroscopy imaging and having 407 markers in total.

Figure 9:
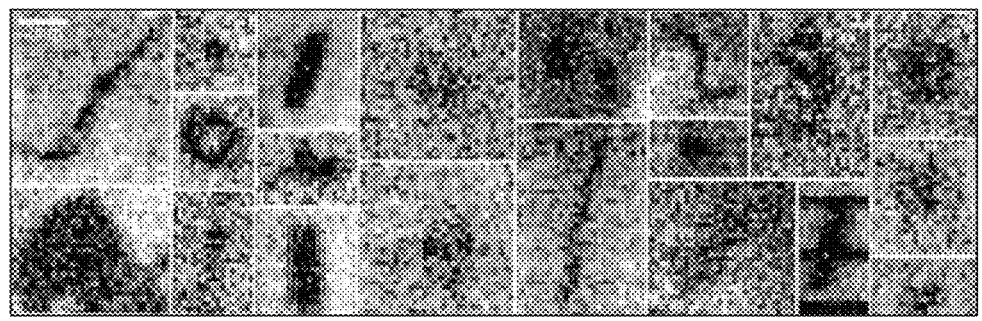
FIG. 9 shows images used for experimental testing of the marker tracking algorithm of FIG. 1.

FIG. 9 shows examples of various different radiopaque markers used in the comparative tests. As can be seen from the figure, the markers varied in size, type, shape, and contrast. The markers ranged in size from approximately 2 mm to approximately 10 mm. True locations of the markers were manually defined by the experimenter on every image. These true locations were then used as the basis for comparison for the algorithms.

For the template matching algorithm in the CBCT images, the templates were automatically constructed by cropping around the known true locations in 10 successive images on either side of the actual image. These 10 images were then averaged together to form the template. Since template matching algorithms depend greatly on the quality of the templates, this method of constructing the template can be considered the best case scenario. For the fluoroscopy images, the algorithm was run with 10 random templates generated by cropping around the known true location. The run that resulted in the lowest error was saved. This also represents the best case scenario for fluoroscopy images. The template matching algorithm used in both cases uses the normalized cross correlation to find the best match between the template and the search space. The search space is set to be the same size as the search space used for the dynamic programming algorithm (in this test, 100×100 pixels), and centered on the true marker location.

Figure 10:
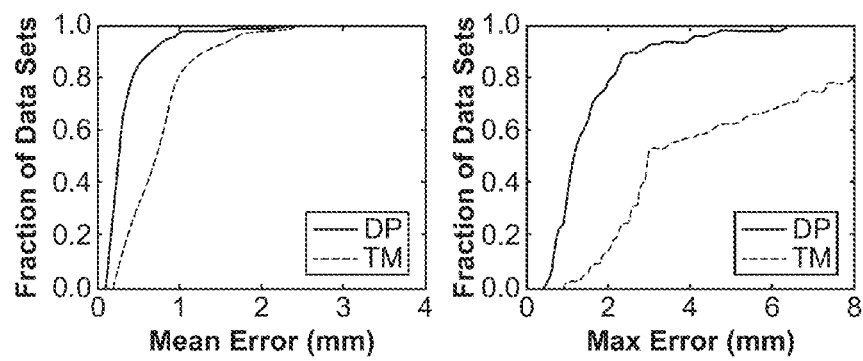
FIGS. 10-13 show test results of experimental testing of the marker tracking algorithm of FIG. 1.
Figure 11:
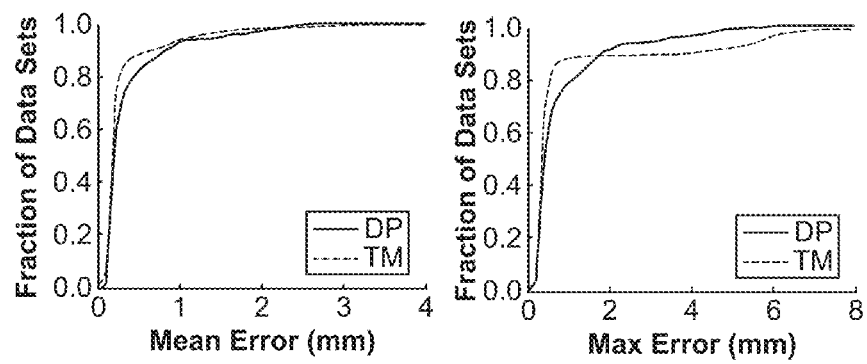

FIG. 10 compares the mean error and the maximum error for both algorithms on the CBCT data sets, while FIG. 11 makes the same comparison on the fluoroscopy images. The figures plot the fraction of data sets with a mean/max error below a certain value. The errors are defined as the distance between the true and outputted marker locations.

These figures show that for fluoroscopy images, the two algorithms perform about equally. However, the template matching algorithm is a best case scenario, taking the best performing run out of 10 different runs. In a clinical situation, the user would not have the luxury to run the algorithm with different initializations multiple times. The results of template matching varied greatly depending on the initial template. On the other hand, dynamic programming is much more robust to the initialized location. As long as the supplied initial location is close to the marker location, the algorithm will be successful. Furthermore, template matching requires the drawing of a bounding box to define the template, while dynamic programming only requires a single initial point.

Figure 12:
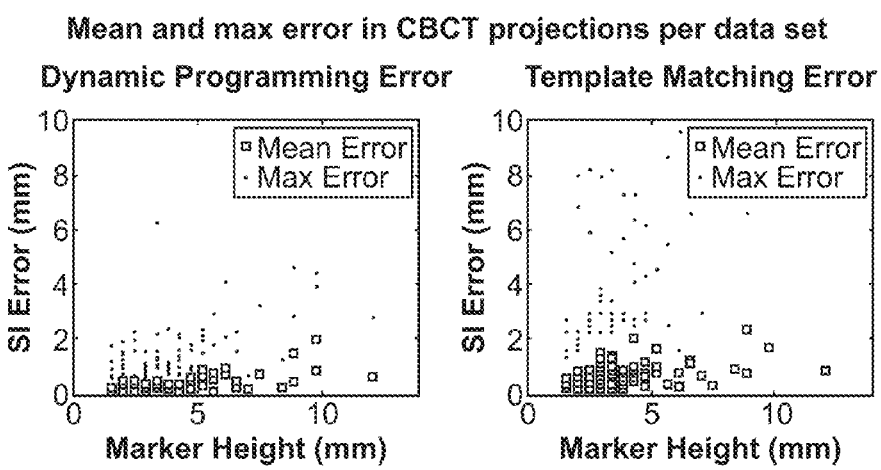
Figure 13:
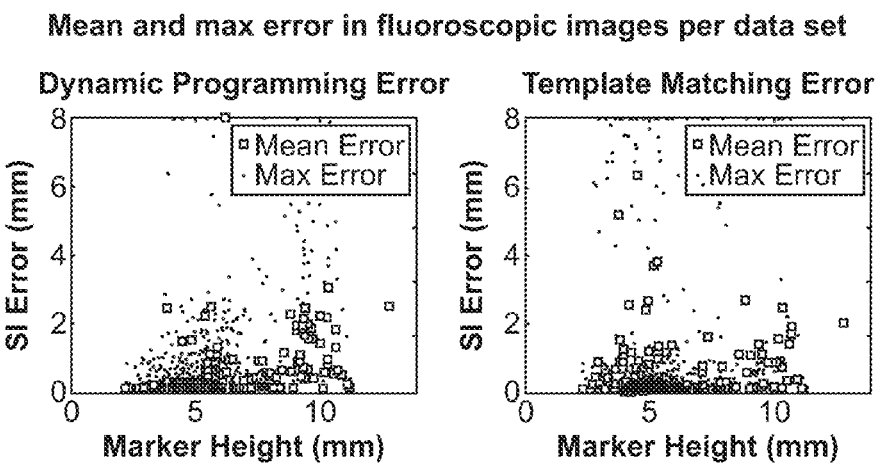

FIGS. 12 and 13 compare the mean and max errors for both algorithms for various marker sizes on the CBCT images and the fluoroscopy images, respectively. Similar results can be seen compared to the earlier analysis. Dynamic programming is much more robust than template matching in the CBCT images, and performs roughly equally in the fluoroscopy images.

These figures also reveal a drawback of dynamic programming. Its performance depends on the size of the markers. For markers smaller than about 8 mm, the algorithm performs very well. For larger markers, its performance begins to degrade. This is because dynamic programming uses a single point to locate markers. Therefore, for larger markers, the predicted point can be anywhere on the marker, and may not necessarily always be right in the middle. Since the error metric is defined as the distance between the outputted location and the true location of the center of the marker, larger markers result in greater errors.

The most likely reason as to why dynamic programming performs much better than template matching in CBCT images, but only performs as well as template matching in fluoroscopy images has to do with the quality of the templates. For the CBCT images, the shape of the markers changes depending on the imager angle. Therefore, it is difficult to find good templates for every image and explains the poorer performance of template matching. Even in the best case scenario, the performance of template matching suffers.

The present disclosure presents a novel marker tracking algorithm that has proven robust to noise and background obstructions as well as to the type, shape, and size of the markers. Also, the inventive tracking algorithm has been shown to perform as well as or better than even a best case scenario of a conventional template tracking algorithm. Furthermore, unlike conventional marker tracking algorithms, the tracking algorithm described herein does not require an initial user template. This greatly decreases the potential for user-generated errors; greatly decreases the input time required by the user; and greatly increases the robustness of the algorithm in the presence of different user inputs, changing image conditions, and image noise.

The novel tracking algorithm described herein is readily applicable for use in a clinical setting to aid physicians in the patient setup process, as well as the gating window selection; and will provide improved reliability, accuracy and efficiency in tracking fiducial markers during radiation therapy. This in turn will result in decreased patient setup times, decreased patient exposure to imaging radiation, and increased efficacy of radiation dose therapy overall.

Although the various features been described with reference to particular embodiments, it will be understood to those skilled in the art that the disclosure herein is exemplary only, and that additional features may be included, if desired, including features that are known and used in the art; and that various other alternatives, adaptations, and modifications may be made within the scope and spirit of the claimed invention.

For example, while the foregoing examples discuss the embodiments relative to target volume movements resulting from respiratory motion, those skilled in the art will appreciate that the principles described herein are also applicable to target volume movements that result from other voluntary muscle movements, as well as involuntary muscle movements (e.g., cardiac or gastrointestinal muscles).

Also, while the foregoing examples are discussed in the context of using pre-planning CT images for initially identifying an approximate 3D marker location, those skilled in the art will appreciate that initial identification of an approximate 3D marker location may also be performed with other registered pre-planning imaging data such as, though not limited to, MR or PET images, or raw imaging data stored in patient records, such as a Digital Imaging and Communications in Medicine (DICOM) record.

In addition, while foregoing examples discuss use of an external surrogate motion tracking system, such as the RPM system, those skilled in the art will appreciate that other examples may be practiced using an internal surrogate motion tracking system, such as the RTRT system.

Also, while the disclosed methods may be performed by executing all of the disclosed steps in the precise order disclosed, without any intermediate steps therebetween, those skilled in the art will appreciate that the methods may also be performed: with further steps interposed between the disclosed steps; with the disclosed steps performed in an order other than the exact order disclosed; with one or more disclosed steps performed simultaneously; and with one or more disclosed steps omitted.

To the extent necessary to understand or complete the subject disclosure, all publications, patents, and patent applications mentioned herein are expressly incorporated by reference herein to the same extent as though each were individually so incorporated. In addition, ranges expressed in the disclosure are considered to include the endpoints of each range, all values in between the end points, and all intermediate ranges subsumed by the end points.

Although particular embodiments have been shown and described, it will be understood that it is not intended to limit the claimed inventions to the preferred embodiments, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed is:

1. A method for localizing a fiducial marker in a medical image comprising:
    obtaining the medical image;
    determining a search window for the medical image; and
    performing an analysis, using an analysis unit, to localize the fiducial marker in the medical image;
    wherein the fiducial marker is localized by the analysis unit without use of a marker template; and
    wherein the act of performing the analysis comprises determining a cost function, the cost function having a component representing a rescaled grayscale intensity at a minima in the search window.

2. The method of claim 1, wherein the search window is determined based on a source-object-imager geometry.

3. The method of claim 1, wherein the search window is determined based on a previously obtained analysis result.

4. A method for localizing a fiducial marker in a medical image comprising:
    obtaining the medical image;
    determining a search window for the medical image, wherein the search window is determined based on a geometry formed by a combination of an object, a source, and an imager; and
    performing an analysis, using an analysis unit, to localize the fiducial marker in the medical image;
    wherein the fiducial marker is localized by the analysis unit without use of a marker template.

5. The method of claim 2, wherein the act of performing the analysis comprises identifying one or more minima in the search window.

6. The method of claim 5, wherein the one or more minima in the search window are identified based on an intensity contrast with a surrounding background intensity.

7. The method of claim 2, wherein the act of performing the analysis comprises determining a cost function.

8. The method of claim 7, wherein the act of performing the analysis further comprises minimizing the cost function.

9. The method of claim 8, wherein the act of minimizing the cost function results in a determination of a marker position for the fiducial marker.

10. The method of claim 9, further comprising repeating the act of performing the analysis to determine an additional marker position for the fiducial marker.

11. The method of claim 10, further comprising comparing the marker position with the additional marker position.

12. The method of claim 7, wherein the cost function comprises a compound cost function.

13. The method of claim 7, wherein the act of performing the analysis comprises maximizing the cost function.

14. The method of claim 4, wherein the act of performing the analysis comprises identifying one or more maxima in the search window.

15. A method for localizing a fiducial marker in a medical image comprising:
    obtaining the medical image;
    determining a search window for the medical image; and
    performing an analysis, using an analysis unit, to localize the fiducial marker in the medical image;
    wherein the fiducial marker is localized by the analysis unit without use of a marker template; and
    wherein the act of performing the analysis comprises determining a cost function, wherein the cost function includes a component representing a distance from a reference location in the search window to a minima in the search window.

16. A method for localizing a fiducial marker in a medical image comprising:
    obtaining the medical image;
    determining a search window for the medical image; and
    performing an analysis, using an analysis unit, to localize the fiducial marker in the medical image;
    wherein the fiducial marker is localized by the analysis unit without use of a marker template; and
    wherein the act of performing the analysis comprises determining a cost function, wherein the cost function includes a component representing a distance between a minima in the search window of the medical image and a minima in another search window of a successive medical image.

17. A method for localizing a fiducial marker in a medical image comprising:
    obtaining the medical image;
    determining a search window for the medical image; and
    performing an analysis, using an analysis unit, to localize the fiducial marker in the medical image;
    wherein the fiducial marker is localized by the analysis unit without use of a marker template; and
    wherein the act of performing the analysis comprises determining a cost function, wherein the cost function includes a first component representing a rescaled grayscale intensity at a minima in the search window, a second component representing a distance from a reference location in the search window to the minima in the search window, and a third component representing a distance between the minima in the search window of the medical image and a minima in another search window of a successive medical image.

18. An apparatus for localizing a fiducial marker in a medical image comprising:
    a processing unit configured to obtain the medical image, and performing an analysis to localize the fiducial marker in the medical image, wherein the processing unit is configured to localize the fiducial marker without use of a marker template; and
    a medium for storing a position of the fiducial marker;
    wherein the processing unit is configured to perform the analysis by determining a cost function, the cost function having a component representing a rescaled grayscale intensity at a minima in a search window.

19. An apparatus for localizing a fiducial marker in a medical image comprising:
a processing unit configured to obtain the medical image, and performing an analysis to localize the fiducial marker in the medical image, wherein the processing unit is configured to localize the fiducial marker without use of a marker template; and
a medium for storing a position of the fiducial marker;
wherein the processing unit is further configured to determine a search window of for the medical image based on a geometry formed by a combination of an object, a source, and an imager.

20. The apparatus of claim 19, wherein the processing unit is configured to perform the analysis by identifying one or more minima in the search window.

21. The apparatus of claim 20, wherein the processing unit is configured to identify the one or more minima in the search window based on an intensity contrast with a surrounding background intensity.

22. The apparatus of claim 19, wherein the processing unit is configured to perform the analysis by determining a cost function.

23. The apparatus of claim 22, wherein the processing unit is configured to perform the analysis further by minimizing the cost function.

24. The apparatus of claim 23, wherein the act of minimizing the cost function results in a determination of a marker position for the marker.

25. The apparatus of claim 24, wherein the processing unit is further configured to repeat the analysis to determine an additional marker position for the fiducial marker.

26. The apparatus of claim 25, wherein the processing unit is further configured to compare the marker position with the additional marker position.

27. The apparatus of claim 22, wherein the cost function comprises a compound cost function.

28. The apparatus of claim 22, wherein the processing unit is configured to perform the analysis further by maximizing the cost function.

29. The apparatus of claim 19, wherein the processing unit is configured to perform the analysis by identifying one or more maxima in the search window.

30. An apparatus for localizing a fiducial marker in a medical image comprising:
a processing unit configured to obtain the medical image, and performing an analysis to localize the fiducial marker in the medical image, wherein the processing unit is configured to localize the fiducial marker without use of a marker template; and
a medium for storing a position of the fiducial marker;
wherein the processing unit is configured to perform the analysis by determining a cost function, wherein the cost function includes a component representing a distance from a reference location in a search window to a minima in the search window.

31. An apparatus for localizing a fiducial marker in a medical image comprising:
a processing unit configured to obtain the medical image, and performing an analysis to localize the fiducial marker in the medical image, wherein the processing unit is configured to localize the fiducial marker without use of a marker template; and
a medium for storing a position of the fiducial marker;
wherein the processing unit is configured to perform the analysis by determining a cost function, wherein the cost function includes a component representing a distance between a minima in a search window of the medical image and a minima in another search window of a successive medical image.

32. An apparatus for localizing a fiducial marker in a medical image comprising:
a processing unit configured to obtain the medical image, and performing an analysis to localize the fiducial marker in the medical image, wherein the processing unit is configured to localize the fiducial marker without use of a marker template; and
a medium for storing a position of the fiducial marker;
wherein the processing unit is configured to perform the analysis by determining a cost function, wherein the cost function includes a first component representing a rescaled grayscale intensity at a minima in a search window, a second component representing a distance from a reference location in the search window to the minima in the search window, and a third component representing a distance between the minima in the search window of the medical image and a minima in another search window of a successive medical image.

33. A method for image analysis comprising:
I) manipulating a set of images to generate at least one approximated search window in each image such that the at least one approximated search window is located in the vicinity of a point of interest in the images;
II) performing a first dynamic analysis, relative to the approximated search windows by: A) identifying within the at least one approximated search window generated in each image one or more contrast points, a contrast point being a local point having an imaging intensity presenting a peak contrast relative to the imaging intensities of points surrounding the local point; B) performing a contrast point characteristic identification step of determining, for each contrast point identified in an individual approximated search window in an individual image of the set of images, at least one of the following contrast point characteristics: i) a distance value between the contrast point and a reference point of the individual approximated search window; ii) an imaging intensity value of the contrast point; and iii) a plurality of distance values measuring the distance from the location of the contrast point in the individual approximated search window to the location of each contrast point in the at least one approximated search window in another image of the set of images; C) repeating the contrast point characteristic identification step for the at least one approximated search window in each image of the image set; D) executing a dynamic programming algorithm to calculate a first resultant point for an individual approximated search window in an individual image of the image set, wherein the dynamic programming algorithm is executed based, at least in part, on input values corresponding to at least one contrast point characteristic value determined during the contrast point characteristic identification step, with an input value being provided for each contrast point identified in the individual approximated search window; E) repeating execution of the dynamic programming algorithm for the at least one approximated search window in each image of the image set; and F) storing the calculated first resultant point of each approximate search window in a data storage unit;
III) manipulating the set of images to generate at least one refined search window in each image such that the at least one refined search window is positioned based on the first resultant point calculated relative to the individual approximated search window for that respective image during the first dynamic analysis;

IV) performing a second dynamic analysis, relative to the refined search windows by repeating the steps of the first dynamic analysis (II), though performing the repeated steps in the second dynamic analysis relative to the refined search windows to calculate and store a second resultant point for each refined search window; and V) performing a convergence judgment step to judge if a convergence has occurred in the image analysis by: G) performing a comparison step of comparing the first resultant point calculated for the at least one approximate search window generated an individual image of the image set with the second resultant point calculated for the at least one refined search window generated in the same individual image to determine if the first resultant point and the second result point are identical; H) repeating the comparison step for the first resultant point and the second resultant point calculated for each image of the image set; I) calculating a convergence percentage by calculating the percent of images of the image set that have a first resultant point and a second resultant point that are identical; and J) judging whether the calculated convergence percentage satisfies a predetermined convergence threshold, with a convergence being deemed to have occurred if the calculated convergence percentage is equal to or above the predetermined convergence threshold, and a convergence being deemed to not have occurred if the calculated convergence percentage is below the predetermined convergence threshold, wherein, if it is deemed in the convergence judgment step (J) that a convergence has occurred, then the identical point identified by the first resultant point and the second resultant point in each image of the image set is deemed to be the point of interest, and wherein, if it is deemed in the convergence judgment step (J) that a convergence has not occurred, then steps (Ill), (IV) and (V) are repeated to calculate and store a third resultant point for each further refined search window, and to judge convergence in the image analysis by comparing the third resultant points to the second resultant points.

34. The method for image analysis according to claim 33, wherein the contrast point is a local minimum point, being a local point having a minimum imaging intensity relative to the imaging intensities of points surrounding the local point.

35. The method for image analysis according to claim 33, wherein the contrast point is a local maximum point, being a local point having a maximum imaging intensity relative to the imaging intensities of points surrounding the local point.

* * * * *